United States Patent [19]
Lee et al.

[11] Patent Number: 5,426,224
[45] Date of Patent: Jun. 20, 1995

[54] MAMMALIAN DNA TOPOISOMERASE II INHIBITOR AND METHOD

[75] Inventors: Kuo-Hsiung Lee; Kenneth F. Bastow, both of Chapel Hill, N.C.

[73] Assignee: The University of North Carolina at Chapel Hill, Chapel Hill, N.C.

[21] Appl. No.: 32,867

[22] Filed: Mar. 18, 1993

[51] Int. Cl.$^6$ .......................................... C07C 233/65
[52] U.S. Cl. ................................. 564/177; 564/174; 564/176; 564/212; 564/213
[58] Field of Search ............... 564/212, 213, 176, 177, 564/174; 514/628, 630, 617

[56] References Cited

FOREIGN PATENT DOCUMENTS 2112131 6/1972 France .

OTHER PUBLICATIONS

Brossi, A., "Bioactive Alkaloids. 4. Results of Recent Investigations with Colchicine and Physostigmine," *J. Med. Chem.* 33(9):2311–2319 (1990).

Capraro, H-G., and A. Brossi, "99. Simple Conversion of Colchicine into Demecolcine," *Helvetica Chimica Acta* 62:965–970 (1979).

D'Arpa, P., and L. F. Liu, "Topoisomerase-targeting antitumor drugs," *Biochim. Biophys. Acta* 989:163–177 (1989).

Liu, L. F., et al., "Cleavage of DNA by Mammalian DNA Topoisomerase II," *J. Biolog. Chem.* 258(24):15365–15370 (1983).

Pastan, I., and M. Gottesman, "Multiple-Drug Resistance in Human Cancer," *New Eng. J. Med.*, May 28:1388–1399 (1987).

Rowe, T. C., et al., "DNA Damage by Antitumor Acridines Mediated by Mammalian DNA Topoisomerase II," *Cancer Res.* 46:2021–2026, 1986.

Tatematsu, H., et al., "Anti–AIDS Agents. 3. Inhibitory Effects of Colchicine Derivatives on HIV Replication in H9 Lymphocyte Cells," *J. Nat. Prod.* 54(2):632–637 (1991).

Yang, L-Y., and J. M. Trujillo, "Biological Characterization of Multidrug-resistant Human Colon Carcinoma Sublines Induced/Selected by Two methods," *Cancer Res.* 50:3218–3225 (1990).

*Primary Examiner*—Shailendra Kumar
*Attorney, Agent, or Firm*—Charles K. Sholtz; Gary R. Fabian; Peter J. Dehlinger

[57] ABSTRACT

A novel antiproliferative drug and methods are disclosed. The drug has the general structural formula:

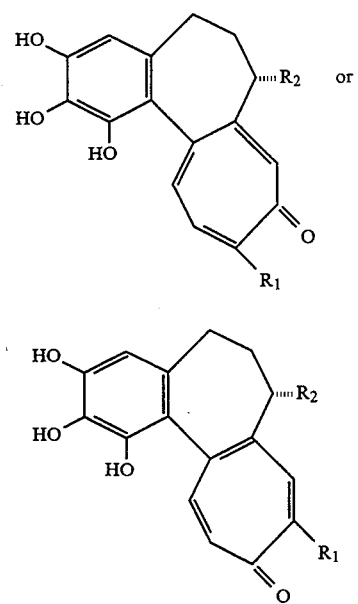

where $R_1 = OR_1'$, $SR_1'$, or $N(R_1'R_1'')_2$, where $R_1'$ and $R_1''$ are H or lower alkyl groups, and $R_2$ is an acylamino, or aroylamino group. The compound is useful for inhibiting cell proliferation in drug-resistant tumor cells. Also disclosed is a method of chemical converting a colchicine derivative to form an active inhibitor of DNA topisomerase II.

2 Claims, 10 Drawing Sheets

WHERE:

$R_1$ = OH, SCH$_3$, NH$_2$, N(CH$_3$)$_2$, N-alkyl,

O-alkyl, O-acyl, N-acyl, OCO—⬡(OH)(OH)(OH), etc.

$R_2$ = NHCOCH$_3$, NHCOCF$_3$, NH$_2$, NHCO—⬡(OH)(OH)(OH),

NHCO—CH=CH—⬡(OH)(OH)(OH), etc

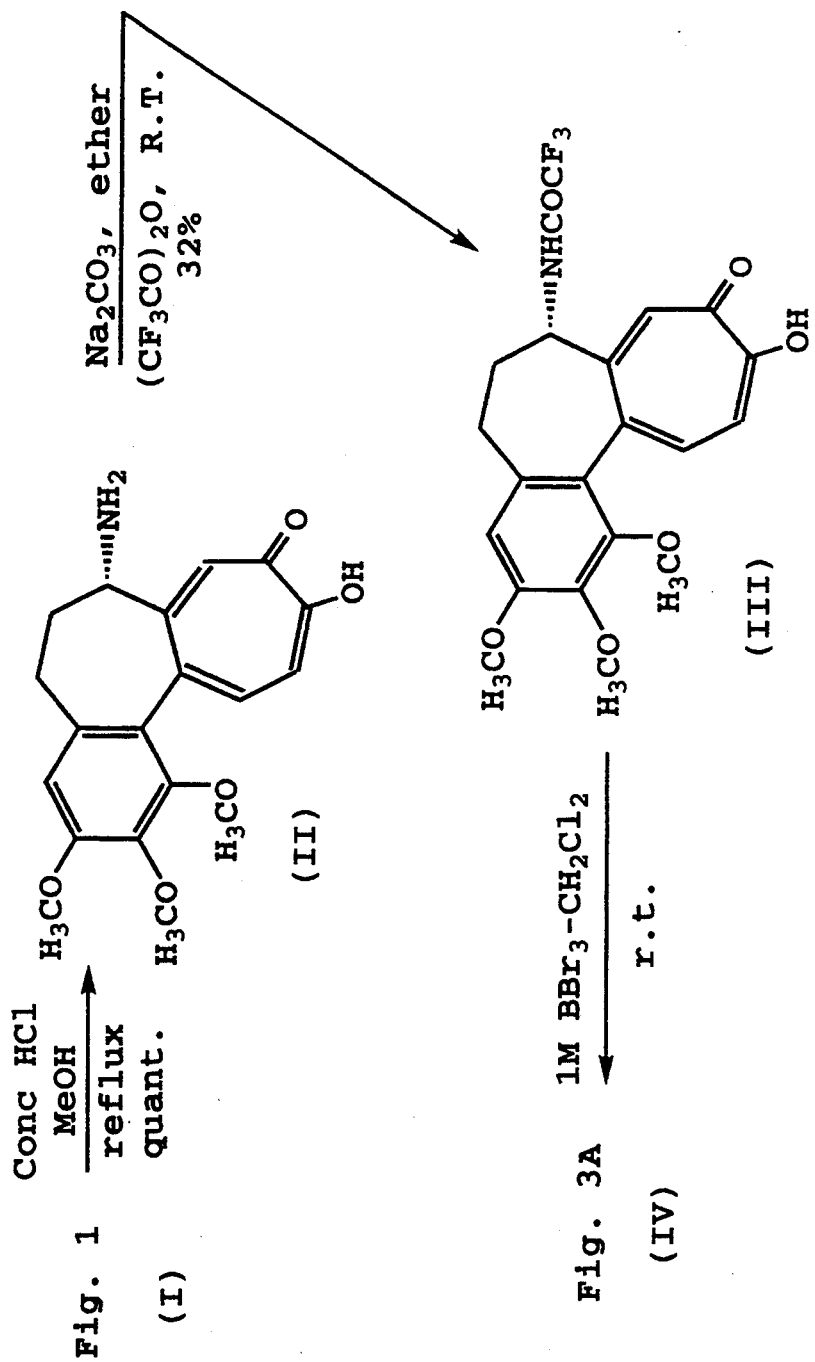

MAMMALIAN DNA TOPOISOMERASE II INHIBITOR AND METHOD

This invention was made with government support under grant No. CA-54508 from the National Cancer Institute. The government has certain rights in the invention.

FIELD OF THE INVENTION

The present invention relates to a colchicine derivative effective to inhibit cell growth in tumor cells.

References

Baum, R, et al., (1989) *Chem. Eng. News*, June 26, p. 7.
Bishop, J. E., et al., (1991) *J. Med. Chem.* 34:1612.
Boer, T. J. D., et al., *Org. Syn. Coll.* IV:25.
Brossi, A. (1990) *J. Med. Chem.* 33:2311–2319.
Capraro, H. G., et al., (1979) *Helv. Chem. Acta* 62:965.
Crumpton, S. C., et al., (1988) *Anticancer Res.* 8:1361.
D'Arpa, P., et al., (1989) *Biochim. Biophys. Acta* 989:163.
Fernholz, V. D. H. (1953) *Angew. Chem.* 65:319.
Goz, B., et al., (1989) *Molec. Pharmacol.* 36:360–365.
Kashiwada, Y., et al., (1993) *J. Pharm. Sci.* submitted.
Leiter, J., et al., (1952) *J. Nat. Canc. Res.* 13:731.
Lettre, V. H., et al., (1972) *Liebigs Ann. Chem.* 758:185–189.
Liu, L. F., et al., (1983) *J. Biol. Chem.* 258:15365–15370.
Liu, L. F., et al., (1981) *Nucl. Acids Res.* 9:3979–3989.
Muzzafar, A., et al., (1990) *J. Med. Chem.* 33:567.
Pastan, I., and Gottesman, M. (1987) *New Engl. J. Med.* May 28, 1388–1393.
Rowe, T. C, et al., (1986) *Cancer Research* 46:2021–2026.
Shearn, M. A. (1987) In: *Basic and Clinical Pharmacology* (Katzung, B. G., ed.) Apple & Lange, Los Altos, Calif., pp. 396–422.
Velluz, L., et al., (1954) *Bull. Soc. Chim.* Fr. pp. 55–757.
Vickery, E. H., et al., (1979) *J. Org. Chem.* 44:4444.
Yang, L.-Y., and Trujillo, J. M. (1990) *Cancer Res.* 50:3218–3225.

BACKGROUND OF THE INVENTION

Colchicine, a major alkaloid of *Colchium autumnale*, is used for treatment of some diseases, such as acute gout, familial Mediterranean fever (FMF), and chronic myelocytic leukemia (Brossi). Colchicine has also been reported as an inhibitor of HIV replication (Baum).

Colchicine exerts its anti-inflammatory and antiproliferative effects through binding to the microtubular protein tubulin preventing tubulin polymerization. Inhibition of tubulin polymerization can lead either to inhibition of leukocyte migration and phagocytosis limiting inflammation associated with acute gout or to inhibition of cellular mitosis decreasing cellular proliferation associated with cancer (Brossi, Shearn).

Treatment of disease with colchicine suffers from two drawbacks. Colchicine doses required to effect its therapeutic actions are usually at toxic or nearly toxic doses. Secondly, cells can become resistant to colchicine by overproducing the p170 glycoprotein drug-efflux pump (Goz).

Numerous chemical modification studies have been performed to enhance colchicine binding to tubulin, while minimizing cellular toxicity (Brossi). For example, selective demethylation at each of four methoxy groups of colchicine (C(1), C(2), C(3), or C(10)) can be performed. Of these four colchine derivatives only 3-demethylcolchicine, a colchicine derivative lacking a methoxy group at C(3), shows good antitubulin binding activity. The structure of colchicine is illustrated in FIG. 1.

Modification of the amide group in colchicine has also been investigated. For example, the ethyl carbamate of deacetylcolchicine is a potent inhibitor of tubulin polymerization activity (Muzaffar). The tropolonic ring of colchicine (ring C in FIG. 1) has been modified replacing the C(10) methoxy group with amines and amino acid esters resulting in biologically active compounds (Leiter).

SUMMARY OF THE INVENTION

In one aspect, the invention includes a compound having the structure:

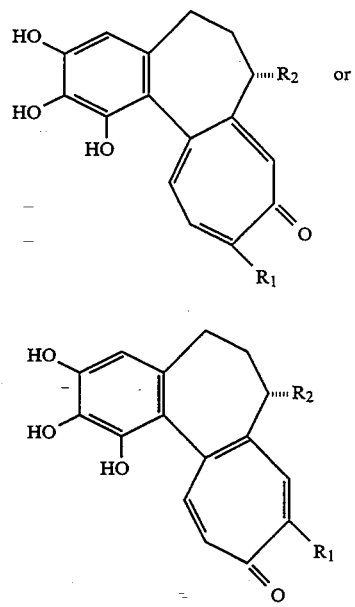

where $R_1 = OR_1'$, $SR_1'$, or $N(R_1'R_1'')_2$, where $R_1'$ and $R_1''$ are H or lower alkyl groups, and $R_2$ is an acylamino, or aroylamino group. In a preferred embodiment, $R_1$ is OH, and $R_2$ is preferably a 3,4,5-trihydroxybenzoyl- or trifluoroacetylamino group.

The compound is an inhibitor of mammalian DNA topoisomerase II activity, as evidenced by (i) a decrease in topoisomerase P4 DNA unknotting activity, at a compound concentration less than about 20 uM, or (ii) the ability of the compound to induce protein-linked DNA breaks in HOS cells when the compound is incubated with the cells at a concentration of at least 10 uM.

The compound also has the ability to inhibit growth of cells which express the p170 glycoprotein drug-efflux pump at a comparable concentration to that required to inhibit the growth of the same cells lacking the p170 drug-efflux pump.

In another aspect, the invention includes a method for inhibiting proliferation of tumor cells which are drug resistant to colchicine, vincristine, etoposide, and doxorubicin compounds, by virtue of the cells' enhanced ability to export the compounds. The method includes exposing the cells to the compound shown above.

Also disclosed is a method of converting a colchicine derivative having C(1), C(2) and C(3) methoxy substituents to an active inhibitor of DNA topoisomerase II activity, as evidenced by the ability of the converted compound to (i) decrease topoisomerase II P4 DNA unknotting activity, at a compound concentration less than about 20 uM, or (ii) induce protein-linked DNA breaks in HOS cells when the compound is incubated with the cells at a concentration of at least 10 uM. The method includes converting the C(1), C(2), and C(3) methoxy substituents to corresponding OH substituents.

These and other objects and features of the present invention will become more fully apparent when the following detailed description of the invention is read in conjunction with the accompanying drawings.

BRIEF DESCRIPTION OF THE FIGURES

FIG. 4 illustrates chemical reactions in the synthesis of TFC;

DETAILED DESCRIPTION OF THE INVENTION

I. Colchicine Derivative

The present invention is directed to a colchicine derivative having antiproliferative activity. In experiments performed in support of the present invention several colchicine derivatives have been discovered that are several orders of magnitude less toxic than colchicine at a concentration effective to inhibit cell growth.

The mechanism of action of these derivatives has been determined to be different from that of colchicine. Whereas colchicine inhibits cell growth by reversible binding to tubulin to prevent microtubule formation, these colchicine derivatives likely inhibit growth in vivo by reversible inhibition of mammalian DNA topoisomerase II activity. Reversible inhibition of mammalian topoisomerase II activity has been associated with a reversible accumulation of protein-linked DNA breaks in cells. Additionally, inhibition of topoisomerase II activity in vitro by these colchicine derivatives is shown.

Figure 1:
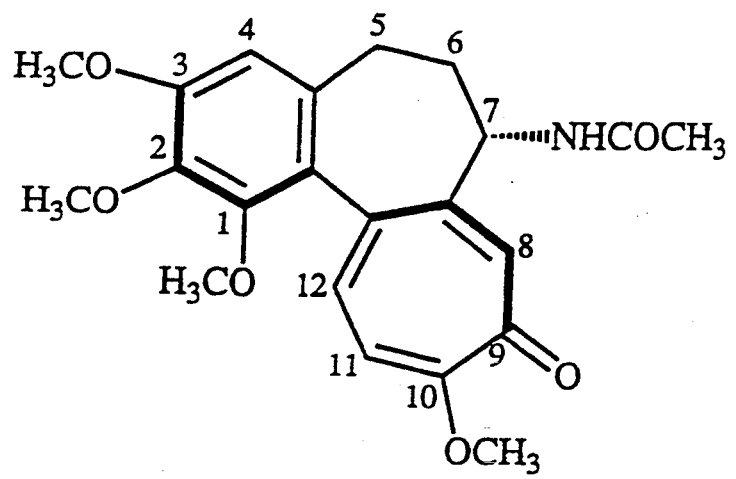
FIG. 1 illustrates the chemical structure of colchicine.

These colchicine derivatives have a three ring structure similar to that of colchicine. Colchicine's chemical structure is illustrated in FIG. 1. As shown, colchicine has methoxy substituents at carbons C(1), C(2), C(3) and C(10) and contains an acetamido group at carbon C(7).

Figures 2A, 2B:
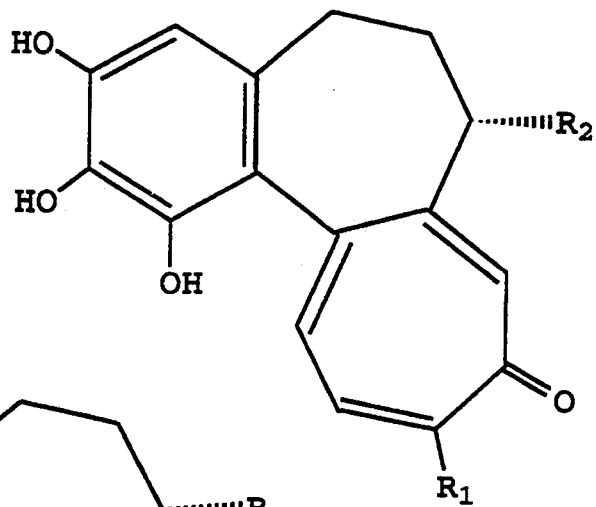
FIGS. 2A and 2B illustrate chemical structures of embodiments of the invention.

General embodiments of colchicine derivatives of this invention are those illustrated in FIGS. 2A and 2B. The derivatives illustrated in FIG. 2A have C(1), C(2) and C(3) methoxy substituents that have been replaced by hydroxyl groups. The C(10) methoxy group can be converted to a hydroxyl group, a thiomethyl group, an amino group, a dimethyl amino group, an alkoxy group, alkyl amino group, O-acyl group, an N-acyl group or a 3,4,5-trihydroxybenzoyl acid group. The acetamido group at C(7) can be NHCOCH$_3$, NHCOCF$_3$, 3,4,5-trihydroxybenzoylamido, or 3,4,5-trimethoxybenzacrylamido groups.

The colchicine derivatives illustrated in FIG. 2B are isomers of the derivatives illustrated in FIG. 2A. The isomers arise from the interconversion of the C(9) ketone group to a C(10) hydroxyl group.

Figure 3A:
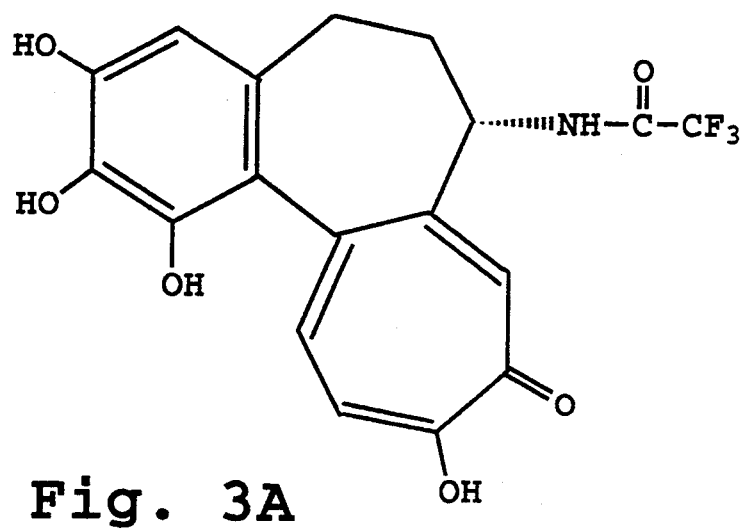
FIGS. 3A and 3B illustrates preferred embodiments of the invention: N-trifluoroacetyl-1,2,3,10-tetrademethyldeactylcolchicine (TFC) (FIG. 3A) and N-(3',4',5'-trihydroxybenzoyl)-1,2,3,10-tetrademethyldeacetylcolchicine (TMBC) (FIG. 3B)
Figure 3B:
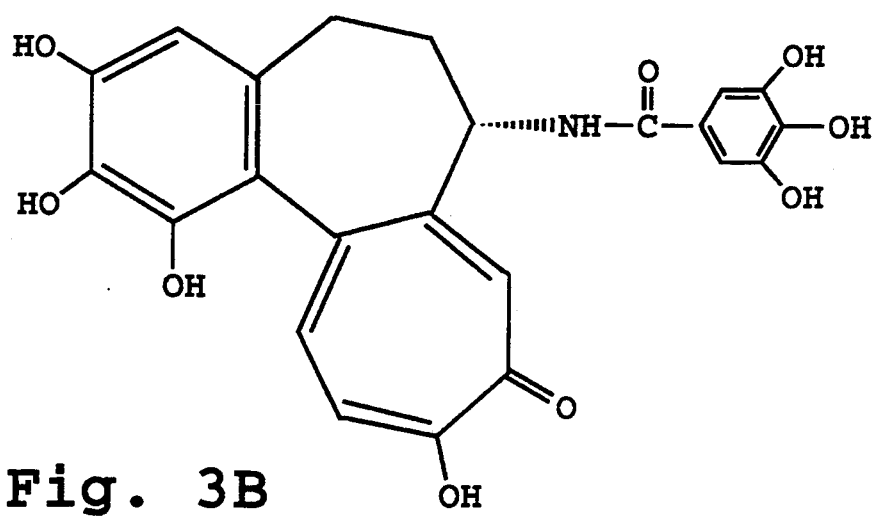

Preferred embodiments are shown in FIGS. 3A and 3B.

In one preferred embodiment of the invention the derivative is N-trifluoroacetyl-1,2,3,10-tetrademethyldeactylcolchicine (TFC) (FIG. 3A). The methoxy groups at carbons C(1), C(2), C(3) and C(10) have been replaced by hydroxyl groups, and the acetamido group has been replaced by a trifluoroacetamido group. In another preferred embodiment the derivative is N-(3',4',5'-trihydroxybenzoyl)-1,2,3,10-tetrademethyldeacetylcolchicine (TMBC) (FIG. 3B). As described for FIG. 3A the four methoxy groups have been replaced by hydroxyl groups. In this case the acetamido group at carbon C(7) has been replaced with a 3,4,5-trihydroxybenzamido group.

II. Colchicine Derivative Synthesis

FIG. 4 illustrates steps in the synthesis of N-trifluoroacetyl-1,2,3,10-tetrademethyldeacetylcolchicine (TFC). Colchicine (compound I) was hydrolyzed in concentrated hydrochloric acid in methanol to form 10-demethyldeacetylcolchicine (compound II) (Fernholz). Product was then acylated with trifluoroacetic acid anhydride to give 10-demethyl-N-trifluoroacetyldeacetylcolchicine (compound III) (Capraro). Compound III was then exhaustively demethylated with boron tribromide in dichloromethane at room temperature to give the desired product (compound IV) (Vickery).

Figure 5A:
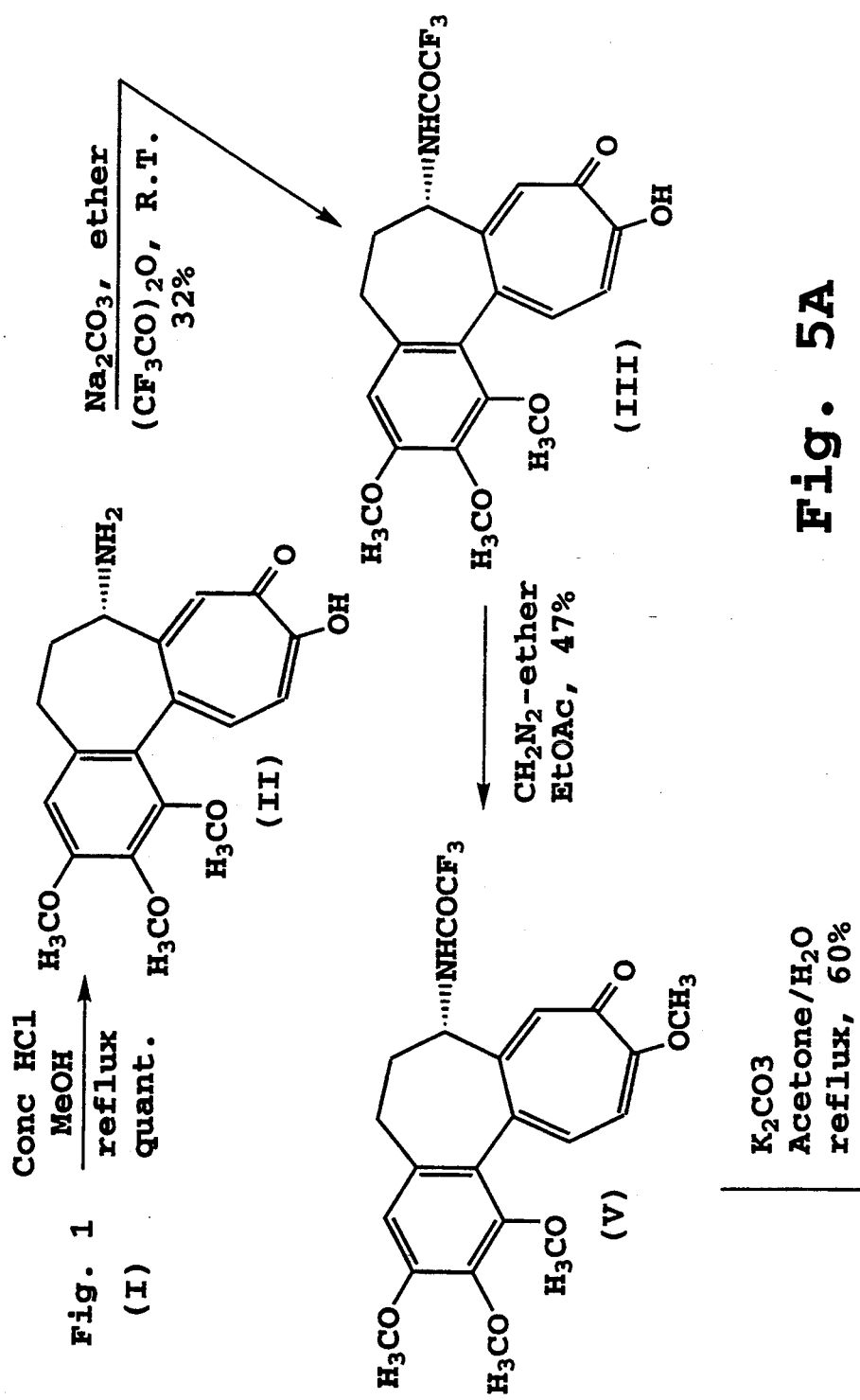
FIGS. 5A and 5B illustrate chemical reactions in the synthesis of TMBC.
Figure 5B:
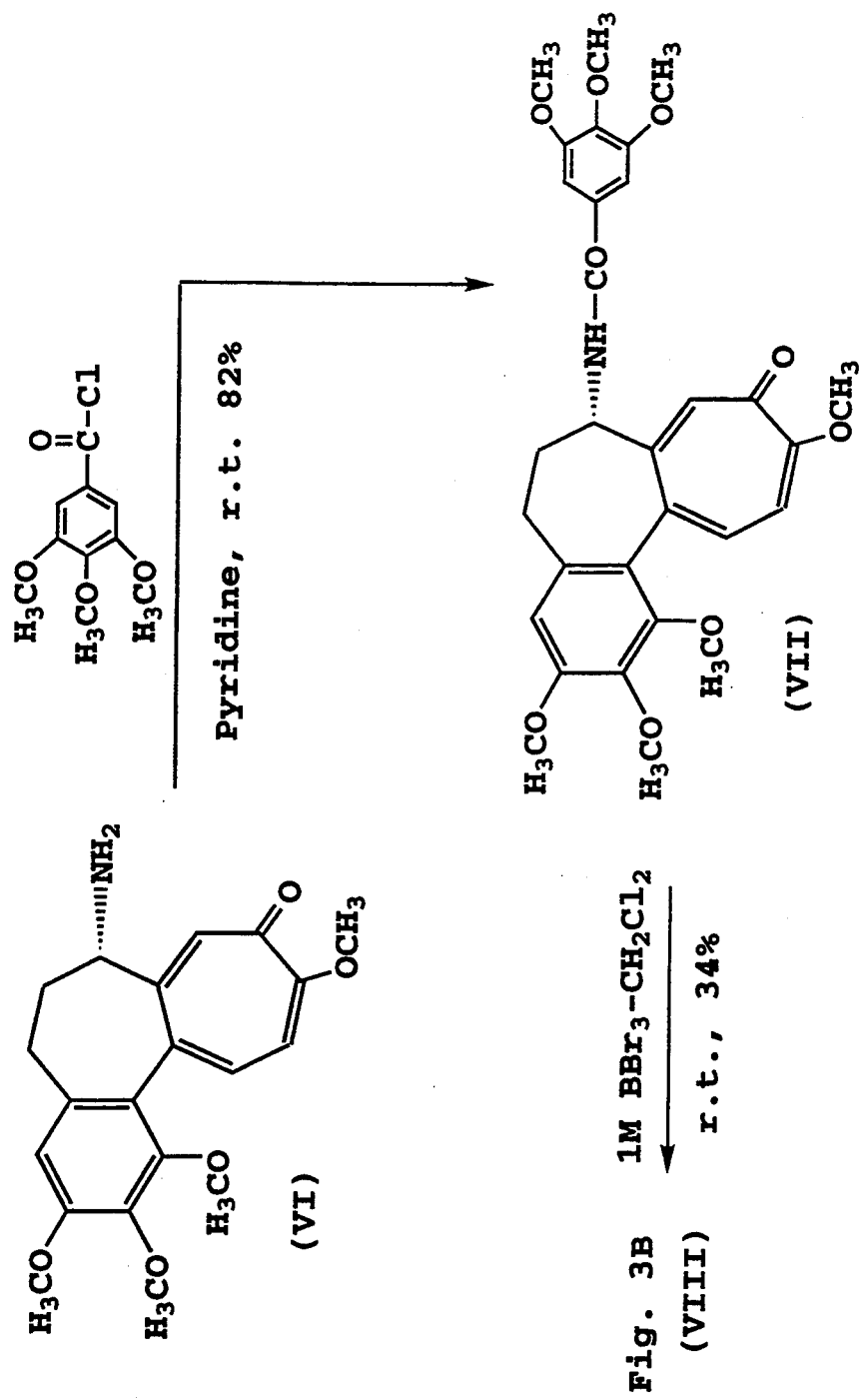

FIGS. 5A and 5B illustrate steps in the synthesis of N-(3',4',5'-trihydroxybenzoyl)-1,2,3,10-demethyldeacetylcolchicine (TMBC). The initial steps of this synthetic procedure are similar to those in FIG. 3. After synthesis of 10-demethyl-N-trifluoroacetyldeacetylcolchicine (compound III), compound III was methylated with diazomethane to form compound V and then hydrolyzed with to generate N-deacetylcolchicine (compound VI) (Capraro).

N-Deacetylcolchicine is condensed with 3,4,5-trimethoxybenzoyl chloride in pyridine at room temperature to form N-(3',4',5'-trimethoxybenzoyl)deacetylcolchicine (compound VII) in good yield. Compound VII was then exhaustively demethylated with boron tribromide in dichloromethane, as described above, to generate product (compound VIII) (Vickery).

Figure 6:
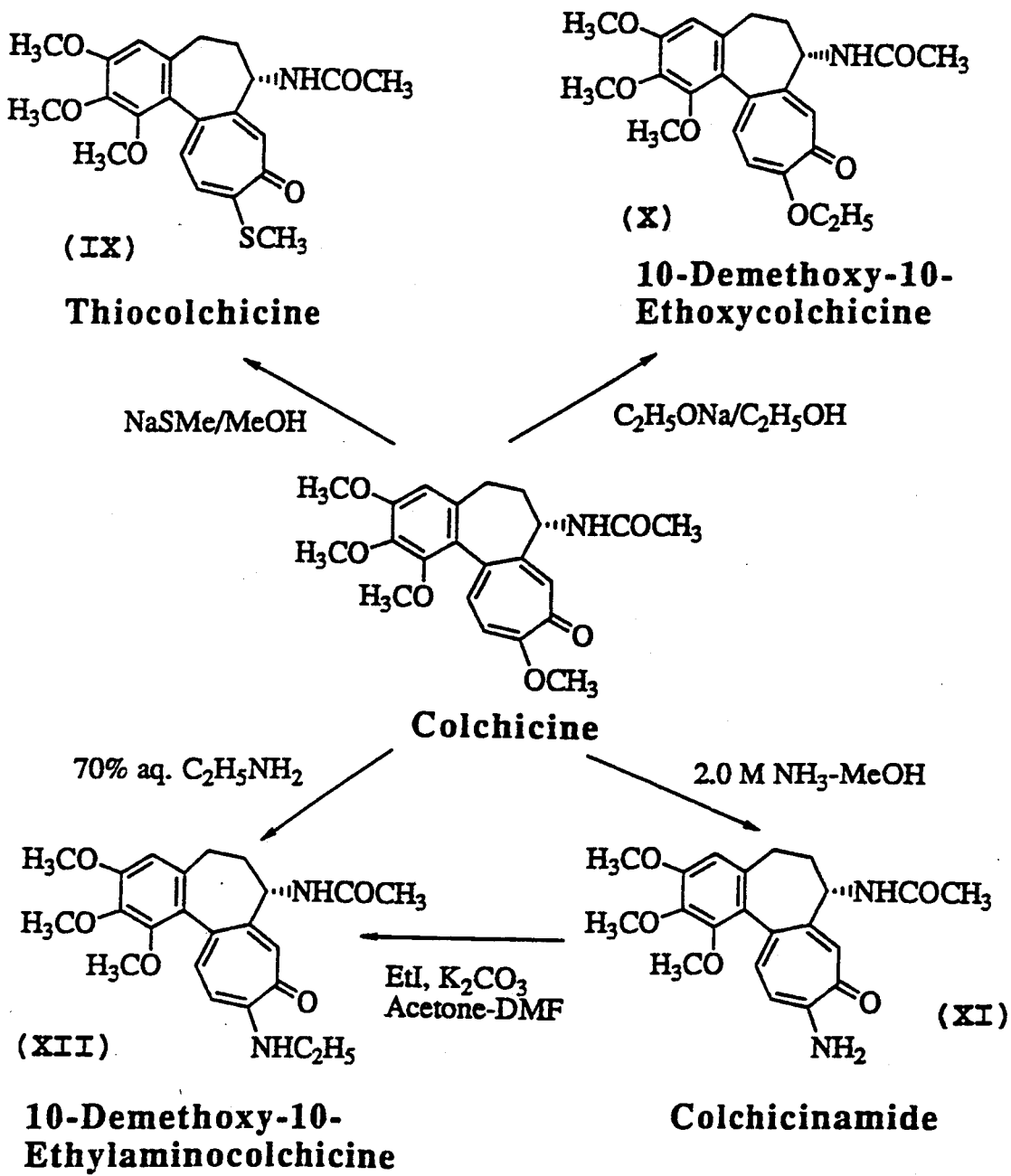
FIG. 6 illustrates chemical reactions in the synthesis of other embodiments of the invention.

FIG. 6 illustrates how alternative colchine derivatives were prepared. For example, thiocholcine (compound IX) was prepared by reacting colchicine with sodium methyl sulfide (Velluz). Another colchicine derivative, 10-demethoxy-10-ethoxycolchicine (compound X) can be prepared by reacting colchicine with sodium ethoxide to generate 10-demethoxy-10-ethoxycolchicine. Colchicinamide (compound XI) can be formed by reaction of colchicine with ammonia in methanol (Lettre). Colchicinamide can be further reacted with ethyliodide to generate 10-demethoxy-10-ethylaminocolchicine (compound XII) (Bishop). Alternatively, 10-demethoxy-10-ethylaminocolchicine (compound XII) can be prepared directly from colchicine by reaction with ethylamine (Lettre).

III. Assays

The effectiveness of colchicine derivatives to inhibit cell growth was determined by investigating growth inhibition of human osteogenic sarcoma (HOS) cells (TE85, clone F-5, ATCC No.: CRL1457). HOS cell growth inhibition by these colchicine derivatives was associated with protein-linked DNA breaks. Since protein-linked DNA breaks have previously been associated with topoisomerase II activity inhibition (Liu, 1983), additional in vitro assays were performed to determine the extent of HOS topoisomerase II activity inhibition by the colchicine derivatives. Additionally, baby hamster kidney (BHK) cell growth inhibition by these derivatives was investigated.

A. Antiproliferative Activity and Cytotoxicity Assays

Cell growth inhibition assays were performed according to published procedures (Crumpton). To HOS cell monolayer cultures of similar density were added varying concentrations of the colchicine derivatives. Control cell replication was followed until approximately three doublings had occured. Control and treated HOS cells were then counted, and concentrations of the colchicine derivatives effective for 50% inhibition of cell replication (EC50) were determined. As illustrated in Table 1, EC50 values of 8.25±0.75 nM, 28 micromolar and 21 micromolar were determined for colchicine, TFC and TMBC, respectively. Growth inhibition of baby hamster kidney (BHK) cells by TMBC, colchicine, and vincristine was also investigated. EC50 values of 28 micromolar, 5 micromolar and 6 nM were obtained for TMBC, colchicine, and vincristine, respectively.

Additionally, the plating efficiencies of the colchicine derivatives were determined. Plating efficiencies are indicative of a compound's cytotoxicity (Goz). Cells plated at low densities were exposed to TMBC or colchicine at varying concentrations for an hour. The compounds were washed away and the plating efficiency was calculated as the per cent cells that were able to form colonies of about 50 or more cells.

As seen in Table 1, the plating efficiency of cells was markedly affected after brief exposure to cytotoxic concentrations of the colchicine derivatives. Concentrations effective to kill 50% of a cell population (LD50) of 14±1 and 18±3 micromolar were determined following a one-hour treatment with TFC and TMBC, respectively. Nanomolar concentrations of colchicine were effective for cytotoxicity.

TABLE 1

TFC, TMBC, Colchicine, and Vincristine EC50 and LD50 Values for HOS and BHK Cells

| Cell Type | TFC | TMBC | Colchicine | Vincristine |
|---|---|---|---|---|
| HOS-EC50 | 28 μM | 21 μM | 8.25 nM | ND |
| BHK-EC50 | ND* | 28 μM | 5 μM | 0.006 μg/ml |
| HOS-LD50 | 14 μM | 18 μM | ND | ND |

*ND = not determined

B. Quantitation of Protein-Linked DNA Breaks

Mammalian DNA topoisomerase II breaks both strands of duplex DNA, and acts as a gate for the passage of a second duplex molecule prior to resealing. By this mechanism it can relax supercoiled DNA and can catenate/decatenate DNA circles. Topoisomerase II therefore plays an important role in both replication and transcription processes (D'Arpa).

Inhibition of mammalian DNA topoisomerase II activity has been associated with the accumulation of protein-linked DNA breaks (Liu, 1983). For example, when topoisomerase II is treated with a protein denaturant a cleavable topoisomerase II-DNA complex is formed. This complex consists of a topoisomerase II molecule attached to a 5'-four base protruding end of each broken DNA strand. The enzyme and nucleic acid are likely linked by a phosphotyrosine bridge. Protein-linked DNA breaks are reversible upon addition of salt or a decrease of temperature from 37° C. to 0° C.

Additionally, certain antitumor drugs, such as anthracyclines, anthacenediones, ellipticines, acridines, and epipodophyllotoxins, have been shown to induce DNA breaks which are mediated by topoisomerase II (Rowe). These protein-linked breaks are reversible upon removal of drug.

Quantitation of protein-linked DNA breaks was performed according to a published procedure (Rowe). DNA in growing cells was labeled by adding methyl-$^3$H-thymidine. Cells were then treated with different concentrations of colchicine, TFC, and TMBC for 30 minutes. Cells were lysed and protein-linked DNA complexes were precipitated by the K-SDS precipitation method (Rowe).

Figure 7A:
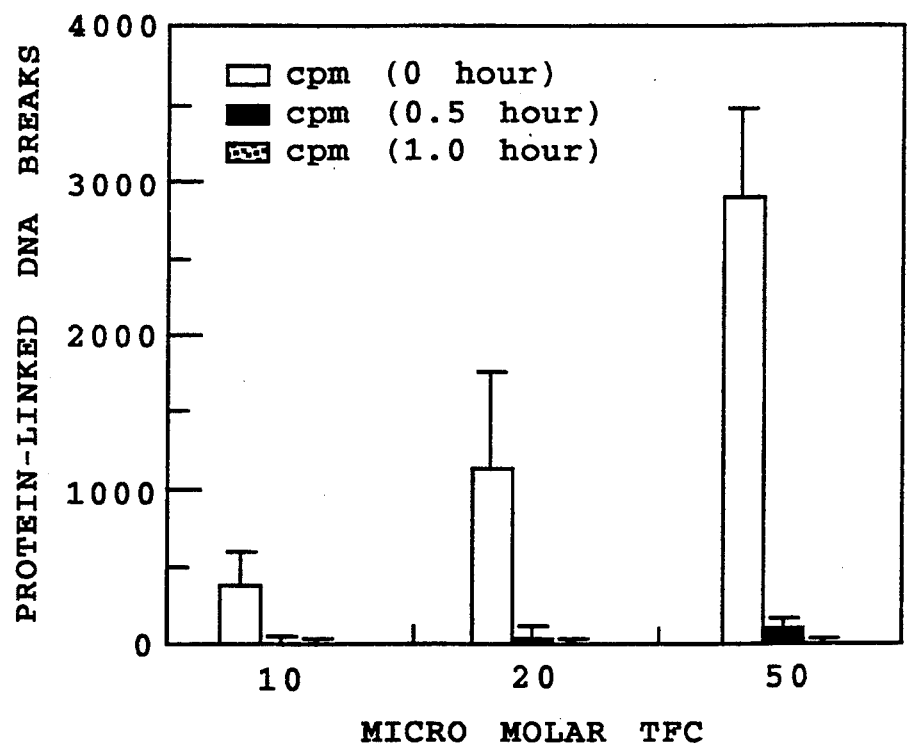
FIGS. 7A and 7B illustrate induction and reversibility of protein-linked DNA breaks in human osteogenic sarcoma (HOS) cells after treatment with TFC (FIG. 7A) or TMBC (FIG. 7B)

FIG. 7A illustrates the induction of protein-linked DNA breaks by increasing concentrations of TFC. TFC induces DNA breaks in a dose-dependent manner in the tested concentration range of 10–50 micromolar. The figure also illustrates the reversibility of the protein-linked DNA breaks upon removal of TFC from the medium. Within half an hour approximately 90% of the protein-linked DNA breaks have reversed and within an hour all the protein-linked DNA breaks have been reversed.

Figure 7B:
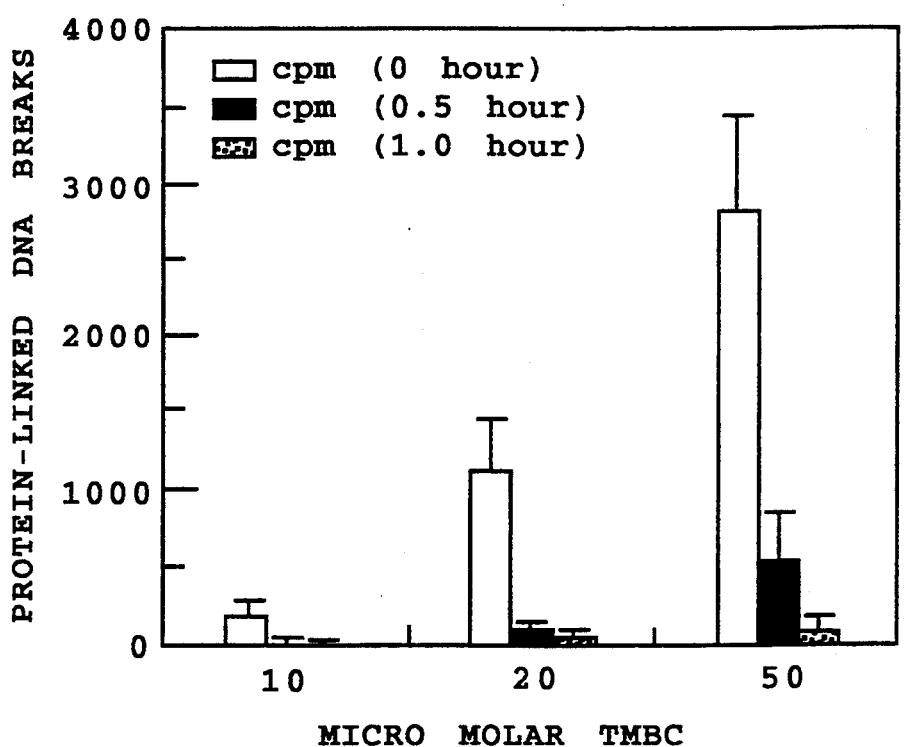

FIG. 7B illustrates the induction and reversibility of protein-linked DNA breaks by increasing concentrations of TMBC. TMBC is almost as effective as TFC for protein-linked DNA break induction. Upon removal of TMBC from the medium the protein-linked DNA breaks are more slowly reversed than for TFC, so that after an hour's time after reversal some protein-linked DNA breaks still remain.

Both TFC and TMBC induce protein-linked DNA breaks in a dose-dependent fashion. In contrast, colchicine at 50 micromolar did not induce protein-linked DNA breaks.

C. Mammalian DNA Topoisomerase II Activity Inhibition

The effect of the colchicine derivatives on mammalian DNA topoisomerase II activity in vitro was investigated. DNA topoisomerase II was purified as described (Kashiwada). Briefly, a 150 mM NaCl extract from Triton X-100-treated HeLa cell nuclei was obtained. Salt was dialyzed and the partially purified enzyme was loaded on a heparin-Sepahrose CL-6B column and batch eluted with a buffer containing increasing salt concentrations.

Enzyme activity was measured using the P4 DNA unknotting assay (Liu, 1981). P4 DNA isolated from bacteriophage P4 consists of monomeric DNA circles with their cohesive ends hydrogen-bonded and contains multiple topological knots. Such highly knotted P4 DNA can be converted to its simple circular form by mammalian DNA topoisomerase II, and can be used as a sensitive assay to detect topoisomerase II activity.

P4 DNA unknotting reactions by topoisomerase II were performed in the absence or presence of potential topoisomerase II inhibitors. The potential topoisomerase II inhibitors tested included TFC, TMBC, the epipodophyllotoxin, VP-16, and colchicine. Products from the cleavage reactions were run out on an agarose gel to determine the extent of P4 DNA unknotting and stained with ethidium bromide.

Figure 8:
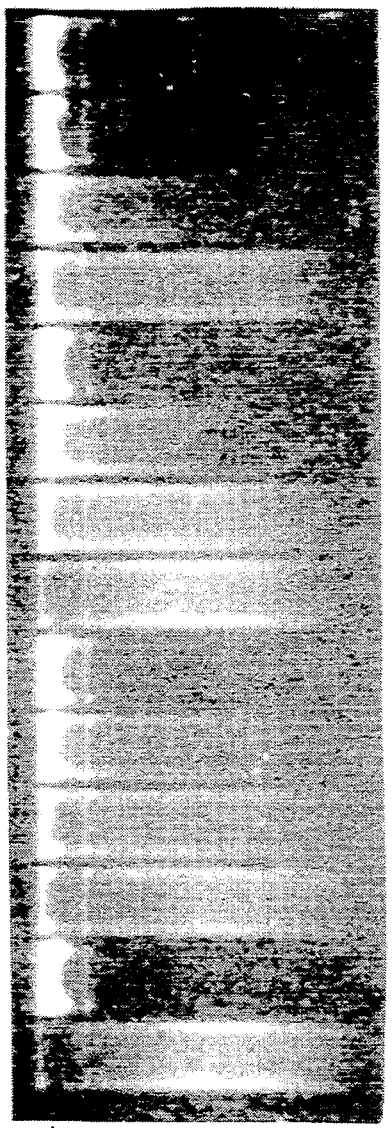
FIG. 8 shows P4 DNA unknotting assays for testing various compounds for inhibition of topoisomerase II activity in vitro.

FIG. 8 illustrates mammalian DNA topoisomerase II P4 DNA unknotting assays performed in the absence (Lane 2) or presence of various putative topoisomerase inhibitors (Lanes 3-14). Lane 1 shows the migration of knotted P4 DNA in the absense of topoisomerase II. Lanes 3-6 show an increase of topoisomerase II activity as the concentration of VP-16 is decreased by 2-fold serial dilutions form 100 to 12.5 micromolar. VP-16 (etoposide) is an epipodophyllotoxin, a toxin known to inhibit topoisomerase II activity (D'Arpa).

Lanes 7-10 show a more striking increase of enzyme activity as the concentration of TFC is decreased by 2-fold serial dilutions from 50 to 6.25 micromolar. Lanes 11-13 show a even more drastic increase of enzyme activity as the concentration of TMBC is decreased by 2-fold serial dilution from 3 to 0.75 micromolar concentrations. Lane 14 shows the effect of cholchicine at a concentration of 200 micromolar on topoisomerase activity.

TFC and TMBC appear to be about 2-fold and 17-fold, respectively, more potent than the epipodophyllotoxin, VP-16. In contrast, colchicine does not appear to inhibit topoisomerase II activity at concentrations as high as 200 micromolar.

IV. Expression of P170 Glycoprotein and Effect on Cell Resistance to Colchicine and Colchicine Derivatives, TFC and TMBC Cells resistant to drugs that are structurally different usually express a 170,000 dalton plasma membrane glycoprotein referred to as p170 or P-glycoprotein (for permeability protein) (Pastan). Cells expressing this glycoprotein can be selected by cell resistance to any of a number of drugs, such as colchicine, vincristine, doxorubicin, vinblastine, vincristine or actinomycin D. The glycoprotein serves to enhance the efflux of drug from a cell without affecting drug import. Rates of drug efflux correlate well with the extent of drug resistance.

In experiments performed in support of the present invention the levels of p170 glycoprotein were determined in HOS cells and in HOS cells resistant to colchicine (HOS colR). HOS colR cells were selected in two succesive steps: first by exposing the cells to 25 nM colchicine and collecting the surviving cells, then by exposing the surviving cells to 75 nM colchicine. As seen in Table 2, the EC50 value of colchicine for HOS colR cells was 315 micromolar, several orders of magnitude higher than that for HOS cells that do not express p170 glycoprotein. The EC50 values for TFC and TMBC remained virtually unchanged at 26 and 28 micromolar, respectively.

BHK-B cells are baby hamster kidney cells that have been selected with 0.05 microgram/ml vincristine and that express p170 glycoprotein. Sensitivity of BHK-B cells to TFC, TMBC and vincristine was investigated. As seen in Table 2, growth of BHK-B cells is inhibited by approximately similar concentrations of TFC and TMBC as BHK cells. However, the concentration of vincristine necessary to inhibit BHK-B cell growth is approximately 50 fold higher than that required for BHK cell growth inhibition. Vincristine is exported by the drug efflux pump, whereas TFC and TMBC are not.

BHK-Ve cells are BHK-B cells which have been treated with 0.03 microgram/ml vincristine in the presence of 5 μM verapamil. Verapamil inhibits drug binding to the p170 glycoprotein drug efflux pump. The EC50 values for TFC and TMBC were 37 and 24 micromolar, respectively. The concentration of vincristine necessary to inhibit BHK-Ve cell growth was increased further to 2.7 μg/ml.

TABLE 2

TFC, TMBC, colchicine, and VP16 EC50 Values for HOS and BHK Cells Expressing p170 Glycoprotein

| Cell Type | TFC | TMBC | Colchicine | Vincristine |
|---|---|---|---|---|
| HOS ColR | 26 μM | 28 μM | 315 μM | ND |
| BHK-B-EC50 | 82 μM | 13 μM | ND | 0.34 μg/ml |
| BHK-Ve-EC50 | 37 μM | 24 μM | ND | 2.7 μg/ml |

Figure 9A:
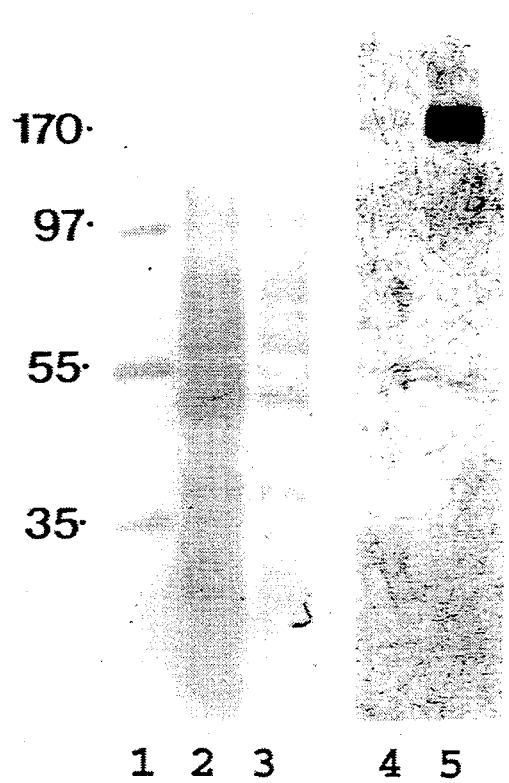
FIGS. 9A and 9B illustrate an immunoblot analysis of p170 glycoprotein expression in HOS cells and in colchicine resistant (colR) HOS cells (FIG. 9A) and induction of protein-linked DNA breaks in HOS cells and HOS colR cells (FIG. 9B).
Figure 9B:
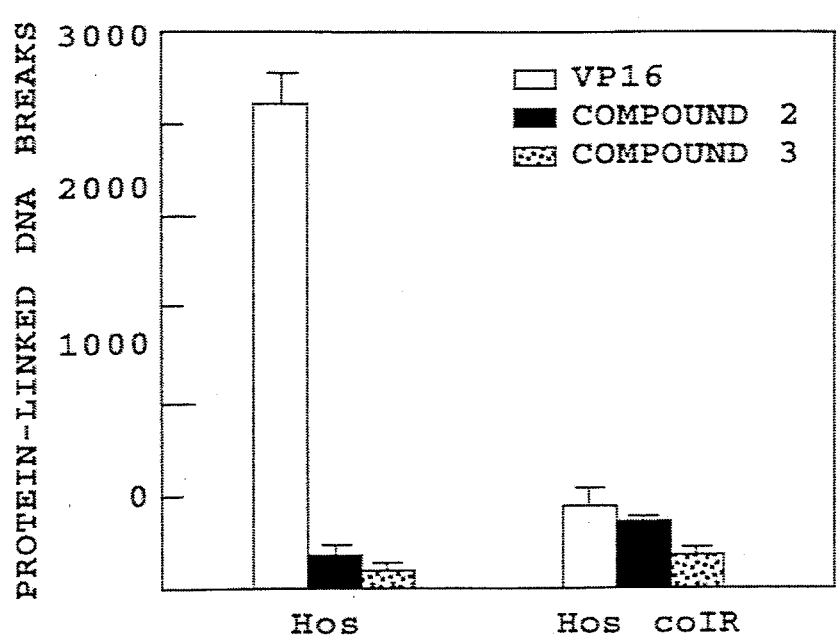

The relationship between colchicine resistance and induction of protein-linked DNA breaks for TFC, TMBC and VP-16 was investigated and results are illustrated in FIGS. 9A and 9B. FIG. 9A shows in Lanes 2 and 3 total plasma membrane protein from HOS and HOS colR cells, respectively, stained by amido black. Lanes 4 and 5 show an immunoblot of the plasma membrane sample which has been reacted with an antibody against p170 glycoprotein for HOS and HOS colR cells, respectively. Lane 1 shows high molecular weight protein standards in the range of 170 to 35 Kda. As expected, only plasma membrane protein samples from HOS colR cells express a protein of about 170 kDa which reacts with the antibody specific for p170.

The amount of protein-linked DNA breaks caused by VP-16, TFC and TMBC were compared in HOS and HOS colR cells to determine whether G170 glycoprotein expression would affect these drugs' ability to induce protein-linked DNA breaks and inhibit topoisomerase II activity. FIG. 9B illustrates these results. In HOS cells, VP-16 at 20 micromolar is very effective to cause protein-linked DNA breaks. Both TFC and TMBC, as described above, can induce protein-linked DNA cleavage to a lesser extent at the same concentration.

In HOS colR cells, VP-16 at 20 micromolar has a limited effect in causing protein-linked DNA breaks, since VP-16 is likely transported out of the cells by the p170 glycoprotein. Neither protein-linked DNA cleavage by either TFC or TMBC appear to be affected by the expression of g170 glycoprotein. Therefore, it is likely that TFC and TMBC use other transport systems for drug efflux.

The following examples illustrate, but in no way are intended to limit the present invention.

Materials and Methods

Example 1

Synthesis of N-trifluoroacetyl-1,2,3,10-tetrademethyl-deactylcolchicine (TFC)

A solution of colchicine (500 mg, 1.25 mmol) in methanol (6.0 ml) containing concentrated HCl (3 ml) was refluxed at 90° C. for 16 hr. Then to the reaction mixture was added 5% NaHCO$_3$ until pH=7. The product was extracted with CHCl$_3$ (20 ml). The combined CHCl$_3$ solution was then washed with brine and dried over anhydrous Na$_2$SO$_4$ to yield 47 mg of amorphous product (compound II) (Fernholz).

Product was then acylated with trifluoroacetic acid anhydride to give 10-demethyl-N-trifluoroacetyl-deacetylcolchicine (Capraro). To a suspension of compound II (97 mg, 0.29 mmol) and Na$_2$CO$_3$ (310 mg, 2.9 mmol) in ether (8 ml) was added trifluoroacetic acid anhydride (0.4 ml) at 0° C. The reaction solution was warmed to room temperature and stirred for 3 h. Water (40 ml) was added to this reaction solution, and the mixture was washed with brine, dried over anhydrous Na$_2$SO$_4$, and concentrated to give 98 mg of compound III.

Product was then exhaustively demethylated with boron tribromide in dichloromethane at room temperature to give the desired product (Vickery). To a solution of compound III in anhydrous methylene chloride cold with dry-ice acetone was added 1M boron tribromide in methylene chloride. The mixture was then stirred at room temperature overnight, added methanol at 0° C. stirred for one hour, and evaporated. Product was purified by Toyopearl chromatography by eluting succesively with water and methanol.

Example 2

Synthesis of N-(3',4',5'-trihydroxybenzoyl)-1,2,3-10-demethyldeacetylcolchicine (TMBC)

The initial steps of this synthetic procedure are similar to those in Example 1. After synthesis of 10-demethyl-N-trifluoroacetyl-deacetylcolchicine (compound III), product was methylated with diazomethane. Diazomethane was synthesized as described (Boer). The diazald kit was assembled as indicated in Aldrich (p. 1709, 1992–1993). A solution of aqueous KOH (6 g/10 ml H$_2$O), carbitol (35 ml), and ether (10 ml) was warmed to 65°–75° C. Then p-tolysulfonylmethylnitrosoamide (21.5 g/125 ml ether) was added through a dropping funnel over 20 minutes. After all the nitrosoamide solution was added, additional ether (60 ml) was placed in the dropping funnel and added at the previous rate. The CH$_2$N$_2$ gas formed was absorbed by the ether.

To a solution of compound III (50 mg) in EtOAc (1.0 ml) was added CH$_2$N$_2$-ether (1.0 ml), and the reaction mixture was stirred for 20 minutes. The reaction solution was then concentrated under vacuum to give 66 mg of product as an oil, which after purification on a preparative TLC plate (eluted with CHCl$_3$—MeOH=9:1) gave 24 mg of compound V.

A solution of compound V (2 g, 4.4 mmol) and K$_2$CO$_3$ (6.8 g, 49 mmol) in acetone (16 ml) was stirred at 60° C. for 2 days. Methanol (30 ml) was added, and the reaction mixture was stirred at 100° C. for 5 h, evaporated, and extracted with CHCl$_3$ (100 ml). The organic layer was washed with brine, dried over Na$_2$SO$_4$, and evaporated to give crude product (1.0 g), which was purified by silica gel chromatography with an eluent of CHCl$_3$—MeOH (93:7) to yield 540 mg of compound VI.

A solution of compound VI (46 mg, 0.13 mmol), pyridine (2.0 ml), and 3,4,5-trimethoxybenzoyl chloride (52 mg, 0.22 mmol) in anhydrous CH$_2$Cl$_2$ was stirred at room temperature overnight and then evaporated to give an oil residue. This oil residue was dissolved in CHCl$_3$ (20 ml), washed with 5% NaHCO$_3$ (20 ml), H$_2$O (20 ml), and brine (20 ml), and evaporated to furnish 84 mg crude product. Separation of this crude product on preparative TLC plates with an eluent of CHCl$_3$—MeOH (9:1) afforded 39.6 mg of compound VII.

Product was then exhaustively demethylated with boron tribromide in dichloromethane at room temperature to give the desired product (Vickery). To a solution of compound VII in anhydrous methylene chloride cold with dry-ice acetone was added 1M boron tribromide in methylene chloride. The mixture was then stirred at room temperature overnight, added methaol at 0° C., stirred for one hour, and evaporated. The residue was separated by Toyopearl chromatography by eluting with water and methanol successively.

Example 3

Antiproliferative Activity Assay

The HOS cell growth inhibition assays were done according to a published procedure (Crumpton). All cells were grown in Eagle's minimium essential medium supplemented with 10% fetal bovine serum. Flasks were seeded at a density of $1 \times 10^3$ cell/cm$^2$ for monolayer cultures or $2 \times 10^4$/ml for suspension cultures. Suspension cultures were used immediately for drug addition after dilution to a suitable starting density, and, about 24 hours after seeding, the compounds to be tested were added to the monolayer cultures. All the test compounds were dissolved in 10% dimethylsulfoxide (DMSO) at concentrations that would give a final DMSO concentrations that would give a final DMSO concentration of 0.1%. Control flasks also contained 0.1% DMSO.

Control cell replication was followed until approximately three doublings had occured. Control and treated cells were counted, and concentrations of the colchicine derivatives for 50% inhibition of cell replication (EC50) were determined. Additionally, the plating efficiencies of the colchicine derivatives were determined. Colonies of about 50 or more cells were counted and the plating efficiency was calculated as the per cent cells that were able to form colonies (Goz).

Example 4

Protein-Linked DNA Breaks Assay

A modified K-SDS precipitation assay was used to quantitate in vivo formation of protein-linked DNA breaks (Rowe). HOS cells were grown in Eagle's medium. The DNA in logarithmically growing cells (about $2 \times 10^5$ cells) was labelled by adding tritiated methyl-thymidine (specific activity: 40 Ci/mmol) into the medium to a final concentration of 0.5 microCurie per ml. After overnight incubation, cells were washed and incubated for another 2 hours at 37° C. The cells were then treated with various concentrations of drugs for 30 minutes. The cells were lysed with 1 ml prewarmed lysis solution containing 1.25% SDS, 5 mM EDTA (pH 8) salmon sperm DNA (0.4 mg/ml).

The lysate was transferred to a 1.5 ml Eppendorf tube and after syringing 8 times through a 22 G 1½ gauge needle, 250 microliter of 325 mM KCl were added. The sample was cooled on ice for 10 minutes and centrifuged at 4° C. The pellet was resuspended in 10 mM Tris-HCl (pH 8)-100 mM KCl-1 mM EDTA and salmon sperm DNA (0.1 mg/ml) and placed at 65° C. for 10 minutes with occasional mixing. The suspension was cooled on ice for 10 minutes and recentrifuged. The pellet was washed again before resuspending in water (65° C.). The suspension was combined with 4 ml scintillation fluid and the radioactivity was determined.

Example 5

Topoisomerase II Activity Inhibition

Topoisomerase II was purified from calf thymus by a known method (Kashiwada). P4 DNA was prepared as described (Liu, 1983). Agarose gel assays for P4 DNA unknotting were performed as follows. Reactions (20 microliters) containing 50 mM Tris-HCl (pH7.5), 100 mM KCl, 10 mM magnesium chloride, 1 mM ATP, 0.5 mM dithiothreitol, 0.5 mM EDTA, bovine serum albumin (30 microgram/ml), 100 ng P4 DNA, one unit of HeLa DNA topoisomerase II, and varying concentrations of topoisomerase II inhibitors were incubated at 37° C. After 30 minutes, reactions were terminated by addition of a solution containing 10% SDS. The samples were electrophoresed through a 1% agarose gel in 90 mM Tris-borate (pH 8.3)-2 mM EDTA buffer (Rowe).

Example 6

Expression of P170 Glycoprotein and Effect on Cell Resistance to Colchicine and Colchicine Derivatives The levels of p170 glycoprotein were determined in HOS cells and in a strain of HOS cells resistant to colchicine (HOS colR). HOS colR cells were selected in two succesive steps, first using 25 nM colchicine then 75 nM colchicine.

Plasma membranes were prepared as described (Yang). Cells were lysed and enucleated. The supernatant was collected and centrifuged at 37,500 rpm for 1 hour using a Ti50 rotor. The pellet was resuspended in 0.5 ml buffer containing 10 mM Tris-HCl, pH 8 containing 75 mM sucrose, 25 mM $MgCl_2$, 1.5 mM EDTA, 5 mM dithiothreitol, 0.15M KCl, and 10 micrograms/ml of the following protease inhibitors: phenylmethylsulfonyl fluoride, leupeptin, benzamidine, aprotinin, and pepstatin. The suspension was diluted with an equal volume of a 81% sucrose solution.

The suspension was layered at the bottom of a discontinous sucrose gradient consisting of equal volumes of 20, 34 and 40% sucrose solution. The gradient was centrifuged at 37,500 rpm at 4° C. using a SW1 rotor. Membrane fractions were collected from the 20/34% and 34/40% interfaces, and recentrifuged.

Fifty-four microgram amounts of HOS and HOS colR plasma membrane samples were electrophoresed using a 7.5% SDS-PAGE gel. HOS and HOS colR sample lanes were stained with amido black. Other HOS and HOS colR sample lanes were trasferred to nitrocellulose. The nitrocellulose was then immunoblotted with P-glycoCHEK ™ C219 from Centocor, Inc. (Malvern, Pa.). C219 is an antibody against p170 glycoprotein. Staining was performed according to manufacturer's recommendations.

Protein-linked DNA breaks assays were performed as described for Example 4 using HOS and HOS colR cells. Cells were treated with 20 micromolar V-16, TFC and TMBC.

Example 7

Synthesis of Thiocolchicine

To a solution of colchicine (500 mg, 1.25 mmol) in water (7.0 ml) was added NaSMe (809 mg, 11 mmol). The reaction mixture was stirred at room temperature for one day. The reaction mixture was extracted with $CHCl_3$ (20 ml). The $CHCl_3$ extract was washed with 1% $HCl-H_2O$, water, and brine until pH=7, dried over anhydrous $NaSO_4$, and evaporated. The residue was purified by silica gel chromatography with an eluent of $CHCl_3$—MeOH (95:5) to give 426 mg thiocolchicine (82%) (Velluz).

Example 8

Preparation of 10-Demethoxy-10-Aminocolchicine (Colchicinamide) from Colchicine

To a solution of colchicine in methanol was added 2.0M ammonia in methanol, and the reaction mixture was stirred at room temperature for 1–2 days. The product was extracted with $CHCl_3$. The $CHCl_3$ solution was then washed with brine, dried over anhydrous $Na_2SO_4$, and evaporated. The residue was purified by silica gel chromatography (Lettre).

Example 9

Preparation of 10-Demethoxy-10-Ethylaminocolchicine by Ethylation of Colchicinamide To a solution of colchicinamide and $K_2CO_3$ in acetone-DMF (2:1) was added EtI. The reaction mixture was refluxed at 65° C. overnight and then filtered. The filtrate was evaporated, and the residue dissolved in $CHCl_3$. The solution of $CHCl_3$ was washed with brine until pH=7, dried over anhydrous $Na_2SO_4$, and evaporated. The residue was purified by silica gel chromatography (Bishop).

While the invention has been described with reference to specific methods and embodiments, it will be appreciated that various modifications and changes may be made without departing from the invention.

It is claimed:

1. A compound having the structure:

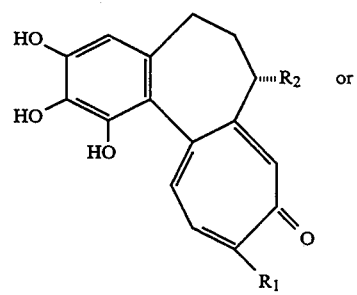

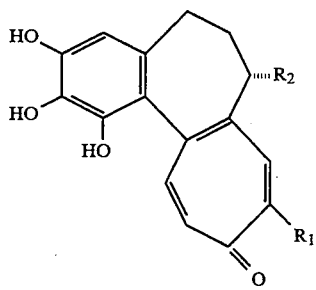
where $R_1 = OR_1'$, $SR_1'$, or $N(R_1'R_1'')_2$, where $R_1'$ and $R_1''$ are H or lower alkyl groups, and $R_2$ is a 3,4,5-trihydroxybenzoyl)amino group.
2. The compound of claim 1, wherein $R_1$ is OH.
* * * * *